(12) United States Patent
Balu-Iyer et al.

(10) Patent No.: US 7,662,405 B2
(45) Date of Patent: Feb. 16, 2010

(54) COMPOSITIONS AND METHODS OF PREPARATION OF LIPOSOMAL MICROPARTICULATE IL-12

(75) Inventors: Sathy V. Balu-Iyer, Amherst, NY (US); Richard B. Bankert, Eden, NY (US); Vivek S. Purohit, Huber Heights, OH (US)

(73) Assignee: The Research Foundation of State University of New York, Amherst, NY (US)

( * ) Notice: Subject to any disclaimer, the term of this patent is extended or adjusted under 35 U.S.C. 154(b) by 12 days.

(21) Appl. No.: 11/502,206

(22) Filed: Aug. 9, 2006

(65) Prior Publication Data

US 2007/0071804 A1    Mar. 29, 2007

Related U.S. Application Data

(60) Provisional application No. 60/706,650, filed on Aug. 9, 2005.

(51) Int. Cl.
  *A61K 9/127*   (2006.01)
  *A61K 45/00*   (2006.01)
(52) U.S. Cl. .................... 424/450; 424/85.2
(58) Field of Classification Search .............. None
  See application file for complete search history.

(56) References Cited

U.S. PATENT DOCUMENTS

| | | | |
|---|---|---|---|
| 4,127,502 A | 11/1978 | Li Mutti et al. | |
| 4,795,806 A | 1/1989 | Brown et al. | |
| 5,580,856 A | 12/1996 | Prestrelski et al. | |
| 5,908,620 A * | 6/1999 | Tu et al. | 424/85.2 |
| 6,033,708 A * | 3/2000 | Kwasiborski et al. | 426/450 |
| 6,423,308 B1 * | 7/2002 | Yarchoan et al. | 424/85.2 |
| 6,544,549 B1 * | 4/2003 | Boni et al. | 424/450 |
| 6,593,294 B1 | 7/2003 | Baru et al. | |
| 6,787,132 B1 * | 9/2004 | Gabizon et al. | 424/85.2 |
| 2001/0043914 A1 * | 11/2001 | Mathiowitz et al. | 424/85.2 |
| 2002/0098192 A1 | 7/2002 | Whitlow et al. | |
| 2002/0132982 A1 | 9/2002 | Balasubramanian et al. | |
| 2003/0118539 A1 | 6/2003 | Fahl et al. | |
| 2003/0176331 A1 | 9/2003 | Rosenblum et al. | |
| 2004/0229793 A1 | 11/2004 | Balasubramanian et al. | |
| 2004/0247661 A1 * | 12/2004 | Michaeli et al. | 424/450 |
| 2005/0136034 A1 * | 6/2005 | Chen et al. | 424/85.2 |
| 2007/0053918 A1 * | 3/2007 | Panzner et al. | 424/450 |

FOREIGN PATENT DOCUMENTS

WO    WO99/55306    11/1999

OTHER PUBLICATIONS

Gabizon et al., *Liposome formulations with prolonged circulation time in blood and enhanced uptake in tumors*. Proc. Natl. Acad. Sci., USA, 85, 6949-6953, 1988.*
Kirby, et. al., *Preparation of liposomes containing factor VIII for oral treatment of haemophilia*. Journal of Microencapsulation, Jan. 1984, vol. 1, pp. 33-45.
Aguilar, et. al., *Phospholipid membranes form specific nonbilayer molecular arrangements that are antigenic*, Sep. 1999, Journal of Biological Chemistry, vol. 274, No. 36, pp. 25193-25196.
Manning, et al., *Stability of Protein Pharmaceuticals*; Pharmaceutical Research, vol. 6, No. 11, 1989, pp. 903-918.
Balasubramanian, et al., *Liposomes as Formulation Excipients for Protein Pharmaceuticals: A Model Protein Study*; Pharmaceutical Research, vol. 17, No. 3, 2000, pp. 344-350.
Braun, et al., *Protein Aggregates Seem to Play a Key Role Among the Parameters Influencing the Antigenicity of Interferon Alpha (IFN-α) in Normal and Transgenic Mice*; Pharmaceutical Research, vol. 14, No. 10, 1997, pp. 1472-1478.
Lenting, P.J., et al., *The light chain of factor VIII comprises a binding site for low density lipoprotein receptor-related protein*; The Journal of Biological Chemistry, Aug. 1999, vol. 274, No. 34, pp. 23734-23739.
Raut, et al., *Phospholipid binding of factor VIII in different therapeutic concentrates*; British Journal of Hematology, 1999, vol. 107, pp. 323-329.

* cited by examiner

*Primary Examiner*—Lorraine Spector
*Assistant Examiner*—Elly-Gerald Stoica
(74) *Attorney, Agent, or Firm*—Hodgson Russ LLP

(57) ABSTRACT

This invention provides methods and compositions for localized delivery of IL-12 to a desired site. The composition comprises liposomes carrying IL-12. The liposomes comprise phosphatidyl choline, phosphatidyl glycerol and cholesterol. The size and composition of the liposomes is such that there is minimal leakage into the systemic circulation. These compositions can be used for delivery of IL-12 to selected sites such as tumors.

18 Claims, 2 Drawing Sheets

Figure 1a
Figure 1b
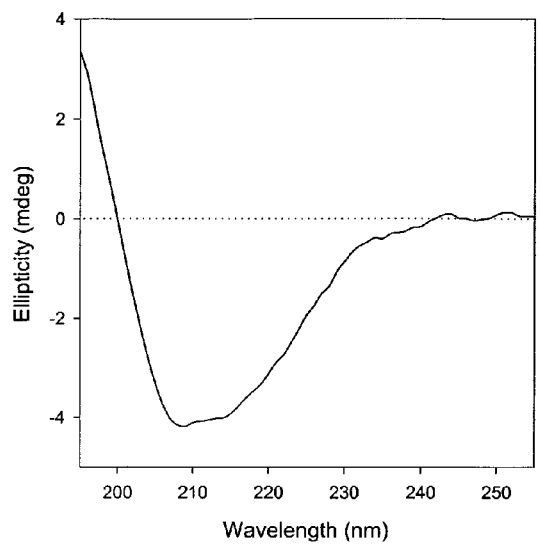
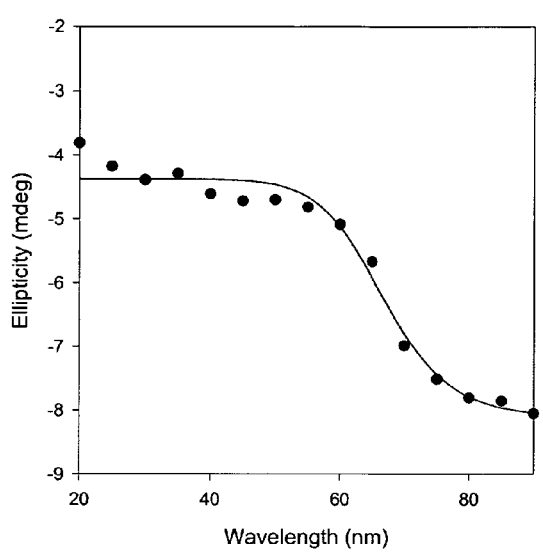
Figure 2
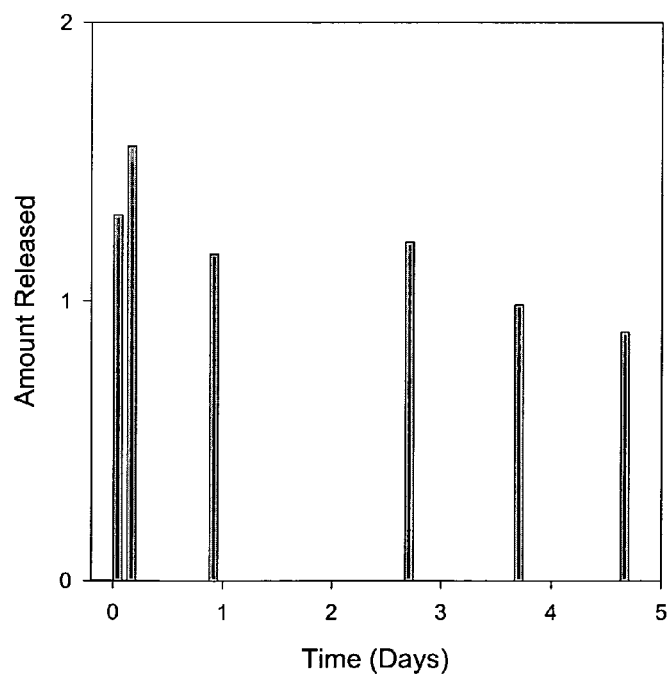

COMPOSITIONS AND METHODS OF PREPARATION OF LIPOSOMAL MICROPARTICULATE IL-12

This application claims priority to U.S. Provisional application No. 60/706,650, filed on Aug. 9, 2005, the disclosure of which is incorporated herein by reference.

BACKGROUND

Interleukin-12 is an immunostimulating cytokine that can stimulate both natural killer cells (nk) and t-cells. Because of these properties, IL-12 has been evaluated in animal models for anti tumor activity. These various animal models have shown partial and complete tumor regression, immunity to rechallenge and improved survival following systemic or peritumoral administration of IL-12. Further, IL-2 is also being used for treatment of a proportion of patients with malignancies such as melanoma and renal cell carcinoma, both alone and in combination with other therapeutic agents. However, the use of IL-12 has not gained wider clinical use because of associated problems including rapid plasma clearance, biodistribution to nonrelevant tissues, and high toxicity.

Delivery of IL-12 encapsulated in liposomes has been considered. Additionally, liposomes have been shown to potentiate a broad array of humoral and cellular immune responses. The imunoadjuvant activity of Liposomes has been well studied that it can stimulate antibody responses against liposome associated protein antigens. Due to their molecular properties, antigens can be attached to the external surface, encapsulated within the internal aqueous spaces or reconstituted within the lipid bilayers of the liposomes. Thus, while delivery of IL-12 via liposomes provides attractive advantages, such delivery has not gained wide acceptance clinically. Therefore, there continues to be a need to develop liposomal compositions carrying IL-12 which improve delivery and have reduced minimal toxicity.

SUMMARY OF THE INVENTION

The present invention provides compositions and methods for localized delivery of IL-12 to desired sites such as a tumor. The compositions comprise liposomes carrying IL-12. The liposomes comprise phosphatidyl choline, phospatidyl glycerol and cholesterol. The acyl chains of the phosphatidyl choline and phosphatidy glycerol are preferably different in length so as to provide for uneven interdigitation. While not intending to be bound by any particular theory, it is believed that: a) high phase transition temperature of PCs of certain hydrocarbon chain lengths offer rigidity and stability in vivo; b) PG carries a negative charge and therefore increases the electrostatic interaction between positive residues of the protein and liposomes; c) Cholesterol enhances the in vivo stability of the liposomes. This results in liposomes which have an increased aqueous volume and therefore are able to deliver a greater amount of IL-12 to the desired site. The size of majority of the liposomes is preferably between than 400 nm to 5 um.

The method of the present invention comprises administering IL-12 to the desired site. For example, IL-12 can be delivered to a tumor by intratumoral injection. In animal studies it was observed that such administration of IL-12 resulted in increased section of IFN gamma, which forms part of the anti-cancer response.

BRIEF DESCRIPTION OF THE DRAWINGS

FIG. 1: a) CD spectrum of rhIL-12 in phosphate buffer at a protein concentration of 50 µg/ml in 0.1 cm pathlength quartz cuvette obtained at 20° C. b) Temperature dependant ellipticity changes of rhIL-12 in MOPS buffer at a concentration of 20 µg/ml in a 1 cm path length quartz cuvette, monitored at 230 nm. Secondary structural transition of rhIL-12 was monitored over the temperature range of 20-90° C. at a heating rate of 60° C./hr. The changes in ellipticity were fit (solid line) using equation 1 described in Example 1 to determine the $T_m$ (68° C.).

FIG. 2: In vitro release profile of rhIL-12 from liposomes in RPMI-40 containing 10% fetal bovine serum determined as described in Example 1.

DESCRIPTION OF THE INVENTION

Figure 3A:
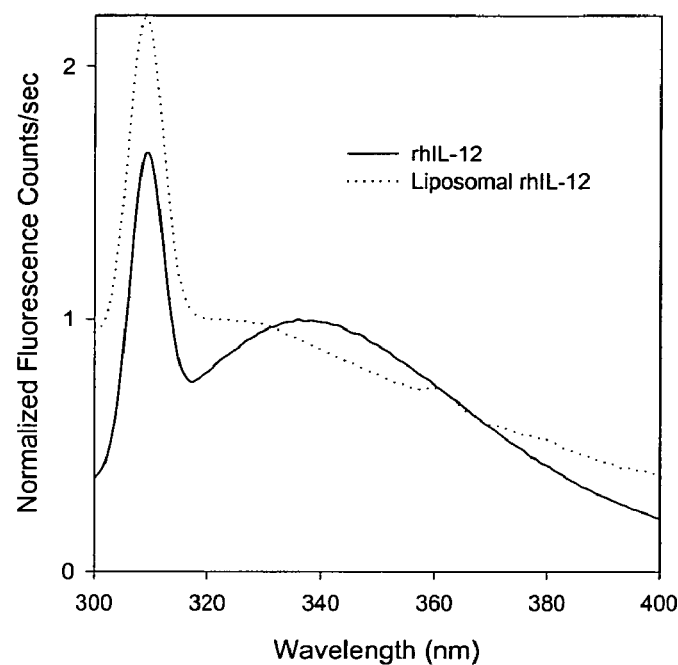
FIG. 3: a) Fluorescence emission spectrum of rhIL-12 (-) and Liposomal rhIL-12 (···) in phosphate buffer at a protein concentration of 2 µg/ml. The emission spectra was acquired over the range of 300-400 µm. The excitation wavelength was set at 280 nm. b) Acrylamide quenching of rhIL-12 (closed symbols) and Liposomal rhIL-12 (open symbols). Stern-Volmer plots were obtained by plotting $F_o/F$ Vs Q. Where, Fo is fluorescence intensity in the absence of quencher, F is fluorescence intensity at a given concentration of quencher (Q). The samples were excited at 280 nm and the emission was monitored at 335 nm. Quenching was achieved by using acrylamide over the concentration range of 0 to 0.8 M

The present invention provides compositions and methods for improved delivery of therapeutic and diagnostic agents. In one embodiment, a method is provided for localized delivery of proteins or peptides. In a further embodiment, a method is provided for the localized delivery of IL-12. The compositions comprise liposomes carrying IL-12.

IL-12 is a heterodimeric cytokine (see Kobayashi et al., 1989, J. Exp. Med. 170: 827). It can be purified from natural sources, produced by chemical synthesis, or produced by recombinant DNA techniques, such as by the expression and subsequent isolation of the IL-12 protein in recombinant host cells. Recombinant technologies are well known in the art. For example, the expression of IL-12 is described in detail in International Patent Application WO90/05 147, published May 17, 1990. The DNA and amino acid sequences of the 30 kD and 40 kD subunits of the heterodimeric human IL-12 are also provided in the above cited international application and in U.S. Pat. No. 5,571,515. As used herein, "interleukin-12" and "IL-12" refer to interleukin-12 (the heterodimeric molecule), its individual subunits, fragments thereof which exhibit IL-12 adjuvant activity, functional equivalents of IL-12.

The liposomes of the present invention comprise phosphatidyl choline, phosphatidyl glycerol and cholesterol. This composition, including the hydrocarbon chain attached to PC and PG, is selected based on the following reasons: a) high phase transition temperature of PCs of certain hydrocarbon chain lengths offer rigidity and stability in vivo; b) PG, which carries a negative charge, increases the electrostatic interaction between positive residues of the protein and liposomes; c) cholesterol enhances the in vivo stability of the liposomes.

The phospholipids PC and PG have two acyl chains. The length of the acyl chains attached to the glycerol backbone varies in length from 12 to 22 carbon atoms. The acyl chains may be saturated or unsaturated. Some non-limiting examples of 12-22 carbon atom saturated and unsaturated acyl chains are shown in Tables 1A and 1B:

TABLE 1A

| Symbol | Common Name | Systematic name | Structure |
|---|---|---|---|
| 12:0 | Lauric acid | dodecanoic acid | $CH_3(CH_2)_{10}COOH$ |
| 14:0 | Myristic acid | tetradecanoic acid | $CH_3(CH_2)_{12}COOH$ |
| 16:0 | Palmitic acid | hexadecanoic acid | $CH_3(CH_2)_{14}COOH$ |
| 18:0 | Stearic acid | octadecanoic acid | $CH_3(CH_2)_{16}COOH$ |
| 20:0 | Arachidic acid | eicosanoic acid | $CH_3(CH_2)_{18}COOH$ |
| 22:0 | Behenic acid | docosanoic acid | $CH_3(CH_2)_{20}COOH$ |

TABLE 1B

| Symbol | Common Name | Systematic name | Structure |
|---|---|---|---|
| 18:1 | Oleic acid | 9-Octadecenoic acid | $CH_3(CH_2)_7CH=CH(CH_2)_7COOH$ |
| 16:1 | Palmitoleic acid | 9-Hexadecenoic acid | $CH_3(CH_2)_5CH=CH(CH_2)_7COOH$ |
| 18:2 | Linoleic acid | 9,12-Octadecadienoic acid | $CH_3(CH_2)_4(CH=CHCH_2)_2(CH_2)_6COOH$ |
| 20:4 | Arachidonic acid | 5,8,11,14-Eicosatetraenoic acid | $CH_3(CH_2)_4(CH=CHCH_2)_4(CH_2)_2COOH$ |

The acyl chains attached to PC are preferably 16 or longer (up to 22). These can be saturated or unsaturated. This provides a phase transition temperature that is higher than the body temperature. If the acyl chains attached to PC are shorter than 16, the liposomes tend to become leaky in vivo and will therefore increase the systemic toxicity associated with IL-12. The acyl chains attached to PG can be from 12 to 22 and can be saturated or unsaturated.

The chains of the PC and the PG are preferably different in length. While not intending to be bound by any particular theory, it is believed that unequal chain lengths in the two phospholipids provide for an uneven boundary thereby increasing the aqueous compartment within the liposome. In a further embodiment, the two acyl chains on the PC or PG can be of different lengths.

In one embodiment, the liposomes comprise Disteroyl Phosphatidyl Choline (DSPC); Dimyristoyl phosphatidyl glycerol (DMPG); and cholesterol. The alkyl chain mismatch between DSPC and DMPG can lead to interdigitation of the bilayers, thereby increasing the encapsulated aqueous volume for higher encapsulation of the protein. The PC:PG:cholesterol can vary between 20:80:10 to 80:20:35. Thus, the ratio of PC to PG can vary between 20:80 to 80:20 and the percentage of cholesterol (as a percentage of PC and PG together) can be between 10 and 35%.

The preparation of liposomes is carried out by routine process. The protein encapsulation procedure involves mild unfolding of the protein and multiple temperature cycle for triggered loading of the protein and for optimal bilayer hydration. For examples, a thin film is prepared by mixing appropriate amounts of lipid solutions in chloroform. Large multilamellar liposomes are prepared by rehydrating the lipid film of appropriate The lipid film is dispersed by gentle swirling and incubated at alternate warm and cold temperatures to ensure proper hydration. The liposomal preparation is then subjected to centrifugation to separate smaller liposomes and free protein from the larger liposomes. It is preferable to use liposomes which are between 400 nm to 5 μm. Thus, in one embodiment, at least 50% of the liposomes are between 400 nm to 5 μm. In another embodiment, at least 90% of the liposomes are between 400 nm to 5 μm. In various further embodiments, at least 50%, 60%, 70%, 80% and 90% of the liposomes have a size greater than 1 um, preferably between 1 μm and 5 μm. The molar ratio between the lipid and the protein can be 1000:1 to 10,000:1. The IL-12 may be encapsulated in the aqueous compartment of the liposomes or may be intercalated within or between the bilayers of the liposomes.

The liposomes of the present invention can be delivered by any standard route. When localized delivery is needed, it is preferable to administer the liposomes at the site of interest. For example for delivery to a tumor, intratumoral injection can be made. Other suitable methods of delivery to the desired site include targeted delivery via use of specific receptor ligands.

The following examples further describe the invention and are intended to be illustrative and not restrictive.

EXAMPLE 1

Materials and Methods

Recombinant human Interleukin-12 (rhIL-12) was obtained as a gift from Genetics Institute (Andover, Mass.). Distearoyl phosphatidylcholine (DSPC) and Dimyristoyl phosphatidylglycerol (DMPG) were obtained from Avanti Polar Lipids (Alabaster, Ala.) and were used without further purification. Cholesterol was obtained from Sigma (St. Louis, Mo.). All other buffer salts and solvents used in the study were obtained from Fisher Scientific (Fairlawn, N.J.) and were used without further purification.

A thin film was prepared by mixing appropriate amounts of lipid solutions in chloroform in a kimax tube and evaporating the chloroform in a Rota-evaporator (Buchi R-200, Fischer Scientific, N.J.). Large multilamellar liposomes were prepared by rehydrating the lipid film of appropriate molar ratios of distearoyl phosphatidylcholine (DSPC), dimyristoyl phosphatidylglycerol (DMPG) and Cholesterol (CHOL) (DSPC:DMPG:CHOL; 80:20:25) with phosphate buffer containing rhIL-12 at 45° C. The lipid film was dispersed by gentle swirling and incubated at 45° C. for 10 min. This was followed by incubation at 4° C. for 15 min. This cycle of alternate incubation at 45° C. and 4° C. was repeated two additional times to ensure proper hydration of the liposomes. The molar ratio between the lipid and the protein was maintained at 2000:1 (0.534 μmoles: 0.267 nmoles) for all experiments. Additional, protein:lipid ratios of 5000:1 and 10000:1 were also used. The liposome associated protein was separated from free protein by centrifugation at 15000 g for 20 minutes at room temperature. The liposome associated protein was obtained as a pellet which was reconstituted in appropriate volume of buffer. Association efficiency was determined by fluorescence spectroscopy utilizing the intrinsic fluorescence of rhIL-12 and by activity assay. Briefly, the fluorescence intensity ($L_T$) of the liposomal preparation prior to separation of free and associated rhIL-12 was measured. After centrifugation the fluorescence intensities of the supernatant ($L_S$) and the reconstituted pellet ($L_P$) were obtained. Amount of rhIL-12 associated with the liposomes was calculated as:

$$\% \text{ Association} = \frac{L_P}{L_T} * 100 \rightarrow \text{Equation 2}$$

The relationship $L_T=L_S+L_P$, was found to be true in all the experiments. The liposomal rhIL-12 was stored at 4° C. and utilized within 24 hours for all experiments.

Particle size of the multi-lamellar liposomes was determined by dynamic light scattering using a Nicomp Model CW 380 particle size analyzer (Particle Sizing Systems, Santa Barbara, Calif.). The instrument was calibrated using 0.258-micron standard latex beads. All measurements were carried out at a temperature of 23° C. with viscosity and refraction index set at 0.933 cP and 1.333 respectively. Data was fitted to an intensity weighted-Nicomp (non-Gaussian) distribution.

CD spectra were acquired on a JASCO-715 spectropolarimeter calibrated with d-10 camphor sulfonic acid. Samples in phosphate buffer (10 mM $Na_2HPO_4$ and 145 mM NaCl, pH-7) containing 50 μg/ml of rhIL-12 in a 1 mm quartz cuvette were scanned from 255 nm to 195 nm for secondary structural analysis. To improve signal quality multiple scans were acquired and averaged. CD spectra of the protein were corrected by subtracting the spectrum of the buffer baseline. Thermal denaturation studies were conducted to monitor the unfolding of rhIL-12 under thermal stress. Samples in MOPS buffer (10 mM MOPS and 155 mM NaCl, pH-7) containing 20 μg/ml of rhIL-12 in a 1 cm quartz cuvette were used for thermal denaturation studies. MOPS buffer was chosen mainly because of its low temperature coefficient ($\Delta pKa/°C.=-0.006$) which ensures minimal pH change at elevated temperatures (1). Hence, observed changes in protein structure in thermal denaturation studies are mainly due to the influence of temperature. Studies were also conducted in phosphate buffer to rule out buffer specific effects. The unfolding profile was acquired at a controlled heating rate of 60° C./hr over the temperature range of 20-90° C. The ellipticity was monitored at 230 nm and the spectrum was obtained from 255-200 nm. The transition temperature ($T_m$) for the unfolding profile was obtained by fitting the data to a sigmoid function (Equation 1) using WinNonlin (Pharsight Corporation, Mountainview, Calif.).

$$Y_{observed} = Y_{native} - \frac{(Y_{native} - Y_{unfolded}) \times T^\gamma}{T^\gamma + T_m^\gamma} \rightarrow \text{Equation 1}$$

where, $Y_{observed}$ is the ellipticity at 230 nm at a given temperature, $Y_{native}$ is ellipticity of the native protein, $Y_{unfolded}$ is the ellipticity of the unfolded protein, $T_m$ is the transition temperature, and $\gamma$ is the fitting function.

In vitro release of rhIL-12 from liposomes was evaluated in RPMI 40 media containing 10% fetal bovine serum. Liposomes containing approx 3 μg of rhIL-12 were mixed with 500 μl of media and placed at 37° C. Samples were taken at 1, 4, 22, 65, 89 and 112 hours. Samples were centrifuged to remove any liposomes and frozen at −80° C. until analysis. The amount of rhIL-12 released was quantified using ELISA for rhIL-12 and activity assay.

Emission spectra of rhIL-12 and liposomal rhIL-12 at a protein concentration of 2 μg/ml in phosphate buffer were obtained using PTI fluorometer (QuantaMaster, Photon Technology International, Lawrenceville, N.J.). The samples were excited at 280 nm and the emission spectrum was obtained from 300-400 nm. A slit width of 4 nm was used on both the excitation and emission paths. A peak observed at 310 nm was due to Raman scattering. This was confirmed by exciting the sample at 260 nm which resulted in disappearance of the peak.

For fluorescence quenching experiments, the samples were excited at 280 nm and the emission was monitored at 335 nm for rhIL-12 and liposomal rhIL-12. Studies were carried out at 20° C. using a slit width of 4 nm on the excitation and emission paths. In order to minimize the contribution due to inner filter effect for samples containing acrylamide, an "I-shaped" cuvette with two different path lengths was used to acquire the fluorescence emission spectra (2). The protein concentration was typically 2 μg/ml in phosphate buffer. Quenching was monitored following successive addition of aliquots of 5 M acrylamide stock solution. The data were analyzed according to the classical Stern-Volmer relationship (2).

Results

Maintenance of the protein activity is critical during the association of the protein to liposomes. To achieve this, a rational structure based approach was undertaken to identify optimal temperature conditions for the liposomal association of the protein with minimal/no loss of activity.

Far-UV circular dichroism spectroscopy was used to monitor the secondary structural features of rhIL-12. The far UV-CD spectrum (FIG. 1a) of rhIL-12 shows negative bands at ~215 nm, and at ~208 nm and a positive band below 200 nm. This suggests that the protein is comprised of both α-helical and β-sheet components. The above observation is consistent with the X-ray crystal structure for human IL-12 which shows that the p40 subunit of human IL-12 exists predominantly as a β-sheet while the p35 subunit exists predominantly as an α-helix (3).

Thermal denaturation studies were conducted to understand the intrinsic stability of rhIL-12 as thermal stress is commonly used to study the folding and stability relationship of proteins (4, 5). Further, knowledge of the intrinsic stability of the protein would aid in identifying optimal conditions for the preparation and handling of liposomal rhIL-12. Shown in FIG. 1b are the ellipticity values at 230 nm, monitored over the temperature range of 20-90° C. following the unfolding of protein at 60° C./hr. No significant changes were observed in the ellipticity values below 50° C. suggesting that the protein undergoes minimal secondary structural changes. At temperatures greater than 50° C. the—ve ellipticity at 230 nm increased progressively due to unfolding of the protein and the midpoint of the transition ($T_m$) was approximately 67° C. Similar results were also obtained in phosphate buffer thereby ruling out any buffer specific effects. These observations indicate that the secondary structural elements of rhIL-12 are not perturbed significantly in response to thermal stress below 50° C. The above observations justified the suitability of the liposomal formation conditions employed for the protein which were conducted at 45° C. where minimal inactivation of the protein due to unfolding can be expected.

The objective of intratumoral administration of IL-12 is to provide cytokine support at the site of action (tumor) for lymphocytes while limiting the systemic toxicity. It is expected that liposomes larger than 400 nm will remain at the site of administration upon subcutaneous administration (6, 7)

The protein was associated with liposomes composed of DSPC:DMPG:CHOL. This composition has the following advantages: a) high phase transition temperature of DSPC which offers rigidity and stability in vivo (8); b) DMPG which carries a negative charge, was included to increase the electrostatic interaction between positive residues of the protein and liposomes; c) cHOL enhances the in vivo stability of the liposomes. The alkyl chain mismatch between DSPC and DMPG can lead to interdigitation of the bilayers (9), thereby increasing the encapsulated aqueous volume for higher encapsulation of the protein. The described preparation procedure gave us consistent association efficiencies of 50-55% to the multilamellar liposomes. In addition to fluorescence spectroscopy association efficiencies were also confirmed by using the activity assay for rhIL-12 (data not shown). The prepared liposomes had a wide distribution of particle sizes consistent with Nicomp (non-Gaussian) distribution. Majority (>90%) of the liposomes had a particle size greater than 1 micron. Presence of even larger (>2 microns) is possible based on the observed fitting parameters.

The in vitro release profile of rhIL-12 from the liposomes is shown in FIG. 2. As can be seen there is a rapid release within the first 4 hours followed by slower release which is sustained for up to 4 days. The initial rapid release is probably due to the protein associated loosely on the surface of the liposomes and can serve as the loading dose for immediate effect on the lymphocytes in the tumor. The sustained slow release can maintain effective low concentrations of rhIL-12 in the tumor for prolonged times.

Fluorescence spectroscopy studies utilizing the intrinsic fluorescence of the protein were done to study the nature of association of rhIL-12 with liposomes. The fluorescence spectrum of rhIL-12 (FIG. 3a) showed an emission maximum of 335 nm. If the association of rhIL-12 with the liposomes is mediated by intercalation of the protein into the lipid bilayers, the emission maximum would undergo a pronounced blue shift with a concomitant increase in quantum yield of tryptophan residues. As can be seen (FIG. 3a) the emission maximum for liposomal rhIL-12 is significantly blue shifted (<325 nm). This is also accompanied by a significant increase in the fluorescence intensity (data not shown) probably due to the incorporation of the fluororescent residues (tryptophan) within a hydrophobic environment. The above spectral changes suggest that a significant amount of the protein is intercalated within or between the liposomal bilayers.

rhIL-12 has 10 tryptophan residues in the molecule and all of them are located in the p40 subunit (β-chain) of the protein (Yoon et al., *Embo J* 19: 3530-41, 2000). The above observations are suggestive of a molecular topology for liposome associated rhIL-12 in which at least the p40 subunit of the protein appears to be intercalated/embedded within the lipid bilayers. An intimate intercalation of the protein within or between the bilayers of the liposomes is of importance as it will lead to a slow release of rhIL-12 from the liposomes.

Figure 3B:
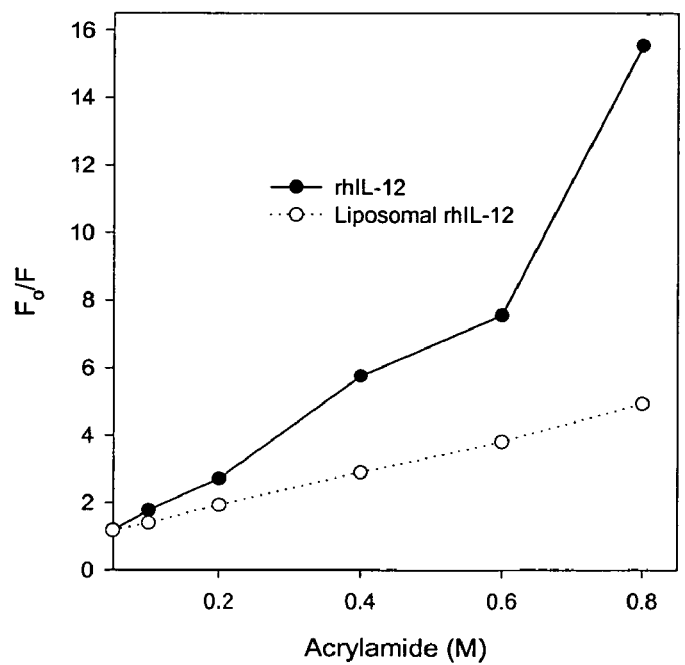

The above observations suggest that a substantial fraction of the rhIL-12 associated with the liposomes maybe sequestered away from the aqueous medium with the liposomes shielding the fluorescent tryptophan residues. Hence, ability of collisional quenchers to quench the fluorescence of liposome associated rhIL-12 would be hindered relative to free rhIL-12. In order to investigate the accessibility of fluorescent residues the collisional quencher acrylamide was added to the liposomal rhIL-12 (FIG. 3b). As observed, the addition of increasing concentration of acrylamide quenched the fluorescence of free rhIL-12 to a greater extent relative to liposomal rhIL-12. This suggests that the liposomes shield a large fraction of the fluorophores within the rhIL-12 molecule which are inaccessible to quenchers. This further confirms that rhIL-12 is intercalated within or between liposomal bilayers.

EXAMPLE 2

This example describes the inn vivo evaluation of LP-IL-12. Studies were carried out in human breast tumor implanted in SCID mice and the xenograft was treated with Liposomal IL-12. The preparation and characterization of liposomal IL-12 (LP-IL-12) is described above. The tumors were implanted into 5 SCID mice and were then treated on Day 5 Post Implant with or without LP-IL-12. The mice were then bled on Day 5 post treatment. The human IFN-gamma was quantitated using ELISA and presence immune responsive cells using immuno histochemistry. The results are shown in Table. 1. As is clear from the table, the LP-IL-12 treated animal show increase in IFN-gamma levels compared to animals receiving no treatment.

TABLE 1

| Treatment | Mouse | IFNG ng/ml |
|---|---|---|
| LP-IL-12 | 4-1 | <.01 |
| | 4-2 | .485 |
| | 4-3 | .473 |
| | 4-4 | .308 |
| | 4-5 | .128 |
| No treatment | 6-1 | <.01 |
| | 6-2 | <.01 |
| | 6-3 | <.01 |
| | 6-4 | <.01 |
| | 6-5 | <.01 |

The xenografts were removed on day 12 post implant (4-1, 4-2) or day 19 post implant (4-3, 4-4, 4.5). Increased levels of CD3+ T cells, CD20+ B cells and CD138+ plasma cells compared to untreated controls were observed. This increase in the inflammatory leukocytes correlated with a decrease in the presence of tumor cells within the xenograft.

REFERENCES

1. T. S. Derrick, R. S. Kashi, M. Durrani, A. Jhingan, and C. R. Middaugh. Effect of metal cations on the conformation and inactivation of recombinant human factor VIII. *J Pharm Sci* 93: 2549-57 (2004).

2. J. R. Lakowicz. *Principles of Fluorescence Spectroscopy*, Kluwer Academic/Plenum Publishers, New York, 1999.

3. C. Yoon, S. C. Johnston, J. Tang, M. Stahl, J. F. Tobin, and W. S. Somers. Charged residues dominate a unique interlocking topography in the heterodimeric cytokine interleukin-12. *Embo J* 19: 3530-41 (2000).

4. C. N. Pace, E. J. Hebert, K. L. Shaw, D. Schell, V. Both, D. Krajcikova, J. Sevcik, K. S. Wilson, Z. Dauter, R. W. Hartley, and G. R. Grimsley. Conformational stability and thermodynamics of folding of ribonucleases Sa, Sa2 and Sa3. *J Mol Biol* 279: 271-86 (1998).

5. A. W. Vermeer and W. Norde. The thermal stability of immunoglobulin: unfolding and aggregation of a multi-domain protein. *Biophys J* 78: 394-404 (2000).

6. C. Oussoren, J. Zuidema, D. J. Crommelin, and G. Storm. Lymphatic uptake and biodistribution of liposomes after subcutaneous injection. II. Influence of liposomal size, lipid composition and lipid dose. *Biochim Biophys Acta* 1328: 261-72 (1997).

7. M. L. Van Slooten, O. Boerman, K. Romoren, E. Kedar, D. J. Crommelin, and G. Storm. Liposomes as sustained release system for human interferon-gamma: biopharmaceutical aspects. *Biochim Biophys Acta* 1530: 134-45 (2001).

8. T. M. Allen, C. Hansen, and J. Rutledge. Liposomes with prolonged circulation times: factors affecting uptake by reticuloendothelial and other tissues. *Biochim Biophys Acta* 981: 27-35 (1989).

9. P. L. Ahl, L. Chen, W. R. Perkins, S. R. Minchey, L. T. Boni, T. F. Taraschi, and A. S. Janoff. Interdigitation-fusion: a new method for producing lipid vesicles of high internal volume. *Biochim Biophys Acta* 1195: 237-44 (1994).

The invention claimed is:

1. A composition comprising multilamellar liposomes carrying IL-12 intercalated within or between the layers thereof, wherein the liposomes comprise phosphatidyl choline (PC), phosphatidyl glycerol (PG) and cholesterol; wherein the acyl chains for the PC and PG are between 12 and 22 carbons in length, the acyl chain length of the PG and the PC are different, and the size of at least 50% of the liposomes is at least 400 nm.

2. The composition of claim 1, wherein the acyl chains of the PC and the PG are saturated.

3. The composition of claim 1, wherein the acyl chains of the PC are between 16 and 22 carbon atoms.

4. The composition of claim 1, wherein the PC is disteroyl phosphatidyl choline (DSPC) and the PG is dimyristoyl phosphatidyl glycerol (DMPG).

5. The composition of claim 1, wherein the at least 90% of the liposomes are between 0.4 to 5 um.

6. The composition of claim 5, wherein at least 50%, 60%, 70%, 80% or 90% of the liposomes are at least 1 um.

7. The composition of claim 1, wherein the ratio of the PC to PG is between 20:80 to 80:20.

8. The composition of claim 6, wherein the cholesterol is between 10-35 wt % of the total PC plus PG.

9. The composition of claim 1, wherein ratio of lipid to IL-12 is between 1,000:1 to 10,000:1.

10. The composition of claim 9, wherein the ratio of lipid to IL-12 is about 2,000:1.

11. The composition of claim 1, wherein the IL-12 is encapsulated within the liposomes.

12. The composition of claim 1, wherein the IL-12 is intercalated within or between the bilayers of the liposomes.

13. A method of preferential localized delivery of IL-12 to a site comprising administering to an individual the composition of claim 1.

14. The method of claim 13, wherein the composition is delivered by subcutaneous injection.

15. The method of claim 13, wherein the composition is delivered by intratumoral injection.

16. The method of claim 13, wherein the site is a tumor.

17. The method of claim 13, wherein the administration of the composition of claim 1 to the site results in a detectible increase in circulating gamma interferon levels.

18. The composition of claim 1, wherein IL-12 has a p40 subunit and at least the p40 subunit of IL-12 is intercalated within or between the layers of the liposomes.

* * * * *

UNITED STATES PATENT AND TRADEMARK OFFICE
CERTIFICATE OF CORRECTION

PATENT NO. : 7,662,405 B2
APPLICATION NO. : 11/502206
DATED : February 16, 2010
INVENTOR(S) : Balu-Iyer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 35 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,662,405 B2
APPLICATION NO. : 11/502206
DATED : February 16, 2010
INVENTOR(S) : Sathy Balu-Iyer et al.

It is certified that error appears in the above-identified patent and that said Letters Patent is hereby corrected as shown below:

Col. 1, lines 8-9 should read,

"This invention was made with Government support under Grant No. CA108970 awarded by the National Institutes of Health. The Government has certain rights in the invention."

Signed and Sealed this
Twenty-ninth Day of January, 2013

David J. Kappos
*Director of the United States Patent and Trademark Office*